US011175286B2

(12) United States Patent
Lee et al.

(10) Patent No.: US 11,175,286 B2
(45) Date of Patent: Nov. 16, 2021

(54) IMMUNOLIPOPLEX NANOPARTICLE BIOCHIP CONTAINING MOLECULAR PROBES FOR CAPTURE AND CHARACTERIZATION OF EXTRACELLULAR VESICLES

(71) Applicant: SPOT BIOSYSTEMS LTD., Palo Alto, CA (US)

(72) Inventors: Ly James Lee, Columbus, OH (US); Kwang Joo Kwak, Dublin, OH (US); Andrew Lee, Columbus, OH (US)

(73) Assignee: SPOT BIOSYSTEMS LTD., Palo Alto, CA (US)

( * ) Notice: Subject to any disclaimer, the term of this patent is extended or adjusted under 35 U.S.C. 154(b) by 0 days.

(21) Appl. No.: 14/992,169

(22) Filed: Jan. 11, 2016

(65) Prior Publication Data
US 2016/0202248 A1    Jul. 14, 2016

Related U.S. Application Data

(60) Provisional application No. 62/124,993, filed on Jan. 9, 2015.

(51) Int. Cl.
| | | |
|---|---|---|
| *G01N 33/53* | (2006.01) | |
| *G01N 33/543* | (2006.01) | |
| *G01N 33/531* | (2006.01) | |

(52) U.S. Cl.
CPC ..... *G01N 33/531* (2013.01); *G01N 33/54346* (2013.01)

(58) Field of Classification Search
None
See application file for complete search history.

(56) References Cited

U.S. PATENT DOCUMENTS

| | | | |
|---|---|---|---|
| 9,541,480 B2 | 1/2017 | Chang et al. | |
| 2004/0112529 A1* | 6/2004 | Karlsson | B01J 19/0093 156/306.6 |
| 2010/0221346 A1* | 9/2010 | Plank | C12N 15/87 424/489 |
| 2011/0059867 A1* | 3/2011 | Kim | C07C 233/20 506/16 |

(Continued)

FOREIGN PATENT DOCUMENTS

CN        103197066 B    12/2015

OTHER PUBLICATIONS

Kwak et al., Formation and Finite Element Analysis of Tethered Bilayer Lipid Structures. Langmuir, 2010, 26:18199-18208.*

(Continued)

*Primary Examiner* — Arthur S Leonard
(74) *Attorney, Agent, or Firm* — Wilson Sonsini Goodrich & Rosati

(57) ABSTRACT

The present invention disclosed a method of fabricating an antibody immunolipoplex nanoparticle (Ab-ILN) biochip and antibody tethered lipoplex nanoparticle (Ab-TLN) biochip. The aforementioned antibody-based lipoplex nanoparticle biochip or the related array contains molecular probes and is applied for detecting the presence of a disease or condition in a subject obtaining a body fluid sample by capturing and identifying both membrane protein and intravesicular DNA/RNA/proteins of extracellular vesicles (EVs).

16 Claims, 8 Drawing Sheets

(56) References Cited

U.S. PATENT DOCUMENTS

| | | | | |
|---|---|---|---|---|
| 2012/0129725 | A1* | 5/2012 | Olsen | C12Q 1/6825 |
| | | | | 506/9 |
| 2014/0094383 | A1 | 4/2014 | Lee et al. | |
| 2014/0134263 | A1* | 5/2014 | Wu | A61K 35/14 |
| | | | | 424/529 |
| 2015/0218651 | A1* | 8/2015 | Lyden | G01N 33/574 |
| | | | | 424/133.1 |

OTHER PUBLICATIONS

Wu et al., Detection of extracellular RNAs in cancer and viral infection via tethered cationic lipoplex nanoparticles containing molecular beacons. Anal Chem. Dec. 3, 2013; 85(23): 11265-11274.*

Tauro et al., Comparison of ultracentrifugation, density gradient separation, and immunoaffinity capture methods for isolating human colon cancer cell line LIMI 863-derived exosomes. Methods 56 (2012) 293-304.*

Logozzi M, et al. (2009) High Levels of Exosomes Expressing CD63 and Caveolin-1 in Plasma of Melanoma Patients. PLoS One 4(4): e5219. doi:10.1371/journal.pone.0005219 (Year: 2009).*

Madhavan et al., Combined evaluation of a panel of protein and miRNA serum-exosome biomarkers for pancreatic cancer diagnosis increases sensitivity and specificity. Int J Cancer. Jun. 1, 2015;136(11):2616-27. doi: 10.1002/ijc.29324. Epub Nov. 25, 2014 (Year: 2015).*

Chinese Patent Application 201610537964.9 Office Action dated Dec. 10, 2018.

\* cited by examiner

IMMUNOLIPOPLEX NANOPARTICLE BIOCHIP CONTAINING MOLECULAR PROBES FOR CAPTURE AND CHARACTERIZATION OF EXTRACELLULAR VESICLES

CROSS-REFERENCE TO RELATED APPLICATIONS

This application claims the benefit of U.S. Provisional Patent Application No. 62/124,993, filed Jan. 9, 2015, which is incorporated by reference in its entirety.

TECHNICAL FIELD OF THE INVENTION

The present invention relates to array biochips consisted of an antibody based capture system for extracellular vesicles (EVs) and liposomal nanoparticles containing molecular probes (MPs), such as molecular beacons and aptamers, to identify nucleic acids and protein content inside the captured EVs. MPs inside the liposomal nanoparticles and antibody or other ligands on the biochip surface can simultaneously capture target EVs from body fluids based on EV surface receptors and identify target messenger RNAs, microRNAs, long non-coding RNAs (lncRNA), circulating genomic DNAs, circulating tumor DNA and/or proteins in the EVs based on MPs as biomarkers. The arrays can also be used to capture and identify viruses and cells.

BACKGROUND OF THE INVENTION

Early and convenient detection has become extremely important against various diseases including cancer, cardiovascular diseases and infectious diseases. The earlier a disease is diagnosed, the more likely it can be cured or successfully managed. Although significant progress has been made in disease diagnosis and treatment, mortality rates of diseases such as cancer, heart failure and AIDS have not changed much in the last several decades. One reason is the lack of sensitive, easy, fast, non-invasive and affordable screening tests for early disease detection. 'Liquid biopsy' by capturing and identifying EVs in human blood or body fluid samples, such as urine, saliva, amniotic fluid and breast milk, has gained a great deal of interest in recent years because of its potential for early and patient-friendly disease detection and monitoring. Surface receptors on EVshave been used for EV separation/isolation via polymer- or magnetic beads-assisted methods where antibodies and other ligands are immobilized onto polymer chains or magnetic particles to capture EVs in body fluids. These methods, however, do not allow the detection of intra-EV contents and mainly serve as an EV isolation step in EV-based assays.

After the EV separation/isolation process, the DNA, RNA and/or protein content in the isolated EVs needs to be collected, and methods, such as proteomic analysis, next generation sequencing (NGS), DNA/RNA microarrays, polymerase chain reaction (PCR) are needed to identify surface antigens on EVs and DNA/RNA/protein targets inside the isolated EVs. The entire sample preparation and target detection process requires more than 30 steps, so it is time consuming, expensive and labor intensive. Furthermore, the separation/isolation and identification/amplification methods are based on the total nucleic acids and proteins collected from all EVs secreted from normal and disease cells. Since EVs secreted from both normal and disease cells may contain similar biomolecules and EVs from disease cells are a minority, particularly in the early stage of the disease, these methods cannot provide high detection sensitivity. They also cannot provide information for individual EVs. New detection methods are needed that can simultaneously identify intra-EV DNA/RNA/protein and EV membrane protein targets at the single EV basis.

Patent application (US 20140094383) demonstrated a biochip with tethered cationic lipoplex nanoparticles (cTLNs) where intra-vesicular RNAs and DNAs are detected by the fusion of negatively charged EVs with positively charged lipoplex nanoparticles tethered on the biochip surface by electrostatic interactions. The same patent application also showed another biochip design where tethered immunolipoplex nanoparticles (iTLN) may capture EVs with target membrane proteins based on antibodies post-inserted onto the tethered lipoplex nanoparticles. However, lipoplex nanoparticles without antibody insertion may also capture EVs, so the iTLN biochip lacks high specificity to identify membrane proteins on EV surface. Herein, we demonstrate new biochip designs to overcome this limitation.

In enzyme-linked immune sorbent assay (ELISA), we have demonstrated that bioactivity of antibodies can be increased by more than 100 times when non-specific binding is minimized by using Protein A connection, polyethylene glycol (PEG) spacers and PEG linkers. These features are included in our new biochip designs.

SUMMARY OF THE INVENTION

The present invention is related to the design of new immunolipoplex nanoparticle (ILN) biochips for capture and characterization of extracellular vesicles (EVs) in blood and other body fluids using antibodies to identify membrane protein targets on EV surface and molecular probes (MPs) in lipoplex nanoparticles to detect intra-vesicular DNA/RNA/protein targets at the individual EV basis. In addition, an array type design can be made, which allows multiplexing detection of membrane protein and intra-vesicular DNA/RNA/protein targets on a single biochip. Furthermore, a whole blood biochip design can also be made to eliminate most sample preparation steps. Theses ILN biochips can also be used to capture and identify viruses and other pathogens.

Utilizing aforementioned design concept, fusion of MP-containing lipoplex nanoparticles allows direct detection of intra-vesicular nucleic acids or proteins contained inside the captured EVs, viruses and other pathogens without any amplification steps.

In one aspect, the present invention disclosed a method of fabricating an antibody immunolipoplex nanoparticle (Ab-ILN) biochip, said method comprises the following steps:

Provide a substrate which comprises glass, silicon wafer, polymer and ceramics; coat gold onto the substrate to form a gold layer on surfaces of the substrate; provide a composition which comprises a lipidic anchor molecule, a linker which comprises a biotin-conjugated thiol molecule with ethylene oxide unites and a lateral spacer; form a self-assembly monolayer with the composition on the gold layer, wherein the self-assembly monolayer containing lipoplex nanoparticles; add an avidin which comprises neutravidin and straptavidin to the self-assembly monolayer, wherein the avidin reacts with the linker to form an avidin-modified surface; bind a protein onto the avidin-modified surface to form an active site, wherein the protein comprises biotin-conjugated Protein A; and perform a reaction with antibodies to have an antibody conjugation on the active site, so as to form the antibody immunolipoplex nanoparticle (Ab-ILN) biochip, wherein the antibody conjugation is a ligands-receptors interaction which comprises avidin-biotin, digoxigenin-anti-Dig, fluorescein-anti-FITC and hapten linkages of antibody molecules.

The aforementioned method is a simple one for preparing an immunolipoplex nanoparticle (ILN) biochip or microarray biochip. In one example, a mixture of lipidic anchor molecule, biotin-PEG-SH and a lateral spacer β-mercaptoethanol (βME) in ethanol were added onto a gold-coated glass substrate to form self-assembly monolayers (SAMs). The biotin-conjugated Protein A was bound on the avidin-modified substrate surface through biotin-avidin interaction. The Protein A-supported antibody could capture the target-antigen specific EVs. Cationic lipoplex nanoparticles (CLNs) containing molecular probes (MPs) were then added onto the chip and reacted with the captured EVs on the substrate surface through vesicle fusion such that the MPs could detect intra-vesicular RNA and DNA targets. Since an antibody is used for capturing EVs and viruses in this design, we named this ILN biochip as Ab-ILN. In addition to antibodies, other ligands such as peptides and carbohydrates can also be bound onto the ILN biochip for capture and detection of EVs, virus and other pathogens.

In one aspect, the present invention also disclosed a method of fabricating an antibody immunolipoplex nanoparticle (Ab-ILN) biochip without coating gold onto a substrate, said method comprises the following steps:

Provide a substrate which comprises glass, silicon wafer, polymer and ceramics; provide a silane which comprises trimethoxy [3-(oxiranylmethoxy)propyl]silane, triethoxy [3-(oxiranylmethoxy)propyl]silane, trimethoxy(methyl) silane, trimethoxy(propyl) silane and triethoxy(propyl) silane; form a self-assembly monolayer with the silane on surfaces of the substrate, wherein the self-assembly monolayer containing lipoplex nanoparticles; bind a protein onto the surfaces to form a active site, wherein the protein comprises Protein A; and perform a reaction with antibodies to have a antibody conjugation on the active site, so as to form the antibody immunolipoplex nanoparticle (Ab-ILN) biochip, wherein the antibody conjugation is a ligands-receptors interaction which comprises avidin-biotin, digoxigenin-anti-Dig, fluorescein-anti-FITC and hapten linkages of antibody molecules.

In another aspect, the present invention disclosed a method of fabricating an antibody tethered lipoplex nanoparticle (Ab-TLN) biochip, said method comprises the following steps:

(1). Provide a substrate which comprises glass, silicon wafer, polymer and ceramics; (2). Coat gold onto the substrate to form a gold layer on surfaces of the substrate; (3). Provide a composition which comprises a tethering molecule, a linker which comprises a biotin-conjugated thiol molecule with ethylene oxide unites and a lateral spacer; (4). Form a self-assembly monolayer with the composition on the gold layer, wherein the self-assembly monolayer containing tethered liposomal nanoparticles; (5). Add an avidin which comprises neutravidin and straptavidin to the self-assembly monolayer, wherein the avidin reacts with the linker to form a avidin-modified surface; and (6). Perform a reaction with antibodies to have an antibody conjugation on the avidin-modified surface, so as to form the antibody tethered lipoplex nanoparticle (Ab-TLN) biochip, wherein the antibody conjugation is a ligands-receptors interaction which comprises complementary DNA/RNA, avidin-biotin, digoxigenin-anti-Dig, fluorescein-anti-FITC and hapten linkages of antibody molecules.

In one example, a mixture of lipidic anchor molecule, biotin-PEG-SH, PEG(2000)-SH spacer and a lateral spacer βME in ethanol was added onto a gold coated glass substrate to form self-assembly monolayers (SAMs). A lipid mixture was used to form the liposomal nanoparticles (LNs). The cationic lipoplex nanoparticles (CLNs) containing molecular beacons (MBs) were tethered on the substrate surface through biotin-avidin interactions. In addition to the biotin-avidin interactions, other ligand-receptors, such as digoxigenin (Dig)-anti-Dig, Fluorescein-anti-FITC or other hapten linkages can also be used to bind LNs onto the TLN biochip surface for EV capture and detection of intra-EV DNA/RNA/protein. The ligand-specific antibody was then added onto the EV-fused TLN biochip for the detection of EV membrane protein. This design allows simultaneous detection of intra-vesicular DNA/RNA/protein targets inside the captured EVs and EV membrane protein targets on the surface of EVs through co-localization analysis. Since an antibody is used for detecting membrane protein targets, we name this TLN biochip as Ab-TLN.

To calibrate the Ab-ILN/TLN biochips, we have designed and prepared EV-like liposomes made of anionic lipopolyplex nanoparticles (ALNs). Various amounts of single strand microRNAs, e.g. miR-21, mixed with a low-cost oligodeoxynucleotide (ODN), such as G3139, were conjugated with phosphate lipids. A typical phospholipids formulation includes 1-palmitoyl-2-oleoyl-sn-glycero-3-phosphocholine (POPC) (68%), Cholesterol (30%) and 1,2-distearoyl-sn-glycero-3-phosphoethanolamine-N-[methoxy(polyethylene glycol)](DSPE-PEG) (2%). Various types and amounts of membrane proteins could be inserted onto the surface of ALNs. These EV-mimic ALNs were loaded onto the Ab-TLN/ILN biochips to serve as an internal standard for chip normalization.

In still another aspect, a method of detecting the presence of a disease or condition in a subject is provided, said method comprises the following steps:

(1). Provide a body fluid sample containing membrane proteins and intra-vesicular DNA/RNA/proteins of extracellular vesicles; (2). Provide an antibody-based biochip which comprises an antibody immunolipoplex nanoparticle (Ab-ILN) biochip and an antibody tethered lipoplex nanoparticle (Ab-TLN) biochip; (3). Contact the body fluid sample with the antibody-based biochip, wherein the membrane proteins and the intra-vesicular DNA/RNA/proteins of extracellular vesicles are captured by molecular probes on the antibody-based biochip, wherein the molecular probes comprises molecular beacons and aptarmer beacons; and (4). Characterize the membrane proteins and the intra-vesicular DNA/RNA/proteins of extracellular vesicles by using instrument which comprises total internal reflection fluorescence (TIRF) microscope, fluorescence microscope, plate reader, microplate reader and portable fluorescence detector, so as to detect the presence of a disease or condition in the subject.

In the aforementioned method of detecting a disease or condition in a subject, we encapsulated MBs in lipoplex nanoparticles (LNs) in order to detect intra-vesicular biomarkers in captured EVs. Other biomolecules, drugs and imaging reagents and their combinations can also be encapsulated in LNs. This biochip can be extended to include a series of microarrays where each small array is consisted of specific antibody, peptide, carbohydrate, or their mixture on the chip surface and specific MB or MB mixture inside the lipoplex nanoparticles.

Such multiplexing array allows capture and detection of many target EVs in a combinatorial design. For example, such a multiplexing array allows capture and detection of >300 RNA targets in a single sample within 2 hours assay time using an automated total internal reflection fluorescence (TIRF) microscope.

The antibody based ILN and TLN biochip designs can be modified to allow for EV capture and detection from a whole blood sample. Here, a droplet of blood is obtained by a finger prick and sucked up by using a heparinized capillary tube. The modified ILN/TLN biochip consists of a double asymmetric membrane filter, such as a polysulfone membrane to remove peripheral blood cells, a track etch membrane or a silicon-based porous elastomeric polymer spacer like polydimethylsiloxane (PDMS) to guide the cell-free serum towards the chip surface, and a syringe with a flow rate controller to drive the blood sample via the double membrane filter onto the chip surface. The EVs in serum are captured and detected by using previously described ILN or TLN designs. We have shown that 20 µL of whole blood could be filtered within 1 minute using a 0.4 µL/s of flow rate.

In conclusion, the present invention disclosed methods of fabricating an antibody immunolipoplex nanoparticle (Ab-ILN) biochip and a method of fabricating an antibody tethered lipoplex nanoparticle (Ab-TLN) biochip. A novel method of detecting a disease or condition in a subject without any amplification steps is also provided.

BRIEF DESCRIPTION OF THE DRAWINGS

FIG. 1. (B) Fluorescence micrographs show that the biochip can distinguish the differences in TTF-1 mRNA level in EVs captured by anti-CD-63 from sera of four Stage I lung cancer patients. FIG. 1 (C) Comparison of TLN and Ab-ILN biochips for the same patients showing good agreement of TTF-1 mRNA expression in EVs. CD-63 is a common membrane protein for exosomes.

FIG. 2. (B) Fluorescence micrographs show that intra-vesicular miR-21 and nucleolin (NCL) membrane proteins identified by our Ab-TLN chip for a pancreatic cancer cell line. The overlapping peaks show co-localization of both miR-21 and NCL protein in the same EVs. Non-specific binding of the second antibody on the biochip was very low, which implies that the observed fluorescence signal was from NCL proteins on the EV surface.

FIG. 3.(B) Two captured individual EVs showing strong miR-21 fluorescence signal. FIG. 3.(C) Total fluorescence intensity of miR-21 rich only, TTF-1 mRNA rich only, and miR-21/TTF-1 rich EVs with CD-63 membrane protein or NCL membrane protein for A549 lung cancer cell line. Both miR-21 and TTF-1 molecular beacons were encapsulated in lipoplex nanoparticles.

FIG. 4. (B) A typical ILN array biochip for 4×6 small areas. FIG. 4. (C) Schematic of ILN microarray biochip connected to a microfluidic setup. Cell culture medium or human body fluids can be brought onto the microarray and EV washing can be carried out.

FIG. 5.(B) A droplet of blood obtained by a finger prick and sucked up by using a heparinized capillary tube. FIG. 5.(C) A blood test conducted on venous blood by using a ILN or TLN biochip. The ILN/TLN biochip consists of a double asymmetric membrane filter to remove peripheral blood cells, micro-channels on silicon-based elastomeric polymer and a syringe with a flow rate controller.

BRIEF DESCRIPTION OF THE PREFERRED EMBODIMENTS

Figure 1:
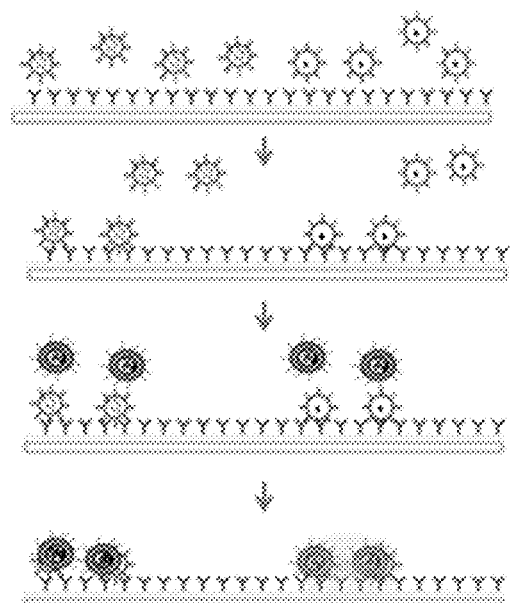
FIG. 1. (A) Schematic of an Ab-ILN biochip design where EVs with specific surface protein are captured by antibody molecules on the chip surface, and their intra-vesicular DNA/RNA/protein content is then identified with lipoplex nanoparticles containing molecular probes (MPs).
Figure 1:
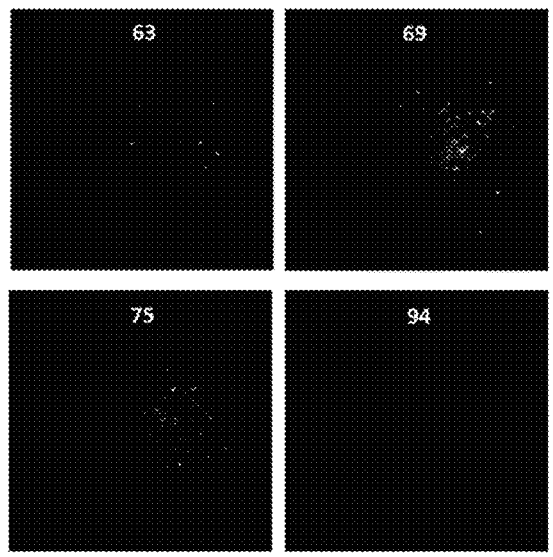
Figure 1:
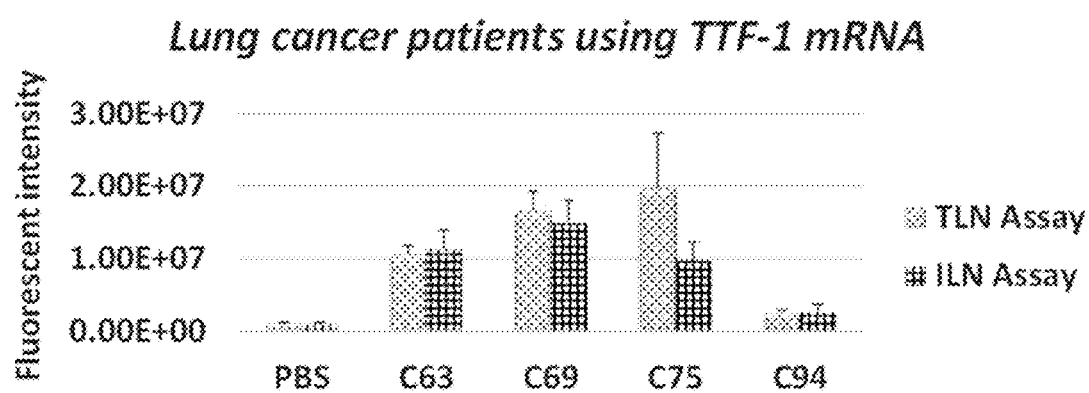

In one embodiment, the invention disclosed a method of fabricating an antibody immunolipoplex nanoparticle (Ab-ILN) biochip, said method comprises the following steps:

Provide a substrate which comprises glass, silicon wafer, polymer and ceramics; coat gold onto the substrate to form a gold layer on surfaces of the substrate; provide a composition which comprises a lipidic anchor molecule, a linker which comprises a biotin-conjugated thiol molecule with ethylene oxide unites and a lateral spacer; form a self-assembly monolayer with the composition on the gold layer, wherein the self-assembly monolayer containing lipoplex nanoparticles; add an avidin which comprises neutravidin and straptavid into the self-assembly monolayer, wherein the avidin reacts with the linker to form an avidin-modified surface; bind a protein onto the avidin-modified surface to form an active site, wherein the protein comprises biotin-conjugated Protein A; and perform a reaction with antibodies to have an antibody conjugation on the active site, so as to form the antibody immunolipoplex nanoparticle (Ab-ILN) biochip, wherein the antibody conjugation is a ligands-receptors interaction which comprises avidin-biotin, digoxigenin-anti-Dig, fluorescein-anti-FITC and hapten linkages of antibody molecules.

In one example of the aforementioned embodiment, the lipidic anchor molecule comprises 20-tetradecyloxy-3,6,9,12,15,18,22-heptaoxahexatricontane-1-thiol (WC14).

In one example of the aforementioned embodiment, the lateral spacer comprises 2-mercaptoethanol, 6-mercaptohexanol and 16-mercaptohexadecanoic acid.

In one example of the aforementioned embodiment, the antibodies were as receptors which comprise moieties for binding to target extracellular vesicles, microvesicles, exosomes and circulating cell-free particles which is selected from one of the group consisting of viruses, bacteria and antigens.

In one example of the aforementioned embodiment, the lipoplex nanoparticles are lyophilized lipoplex nanoparticles.

In one example of the aforementioned embodiment, the lipoplex nanoparticles further comprises reagents which comprise molecular beacons, quantum dots, messenger RNA, microRNA, lncRNA, genomic DNA, circulating tumor DNA, drug, DNA/RNA, magnetic particles, Au nanoparticles and proteins.

In one example of the aforementioned embodiment, the antibody immunolipoplex nanoparticle (Ab-ILN) biochip is applied for finger prick capillary blood assay.

In a second embodiment of the invention, the present invention also disclosed a method of fabricating an antibody immunolipoplex nanoparticle (Ab-ILN) biochip without coating gold onto a substrate, said method comprises the following steps:

Provide a substrate which comprises glass, silicon wafer, polymer and ceramics; provide a silane which comprises trimethoxy [3-(oxiranylmethoxy)propyl]silane, triethoxy [3-(oxiranylmethoxy)propyl]silane, trimethoxy(methyl) silane, trimethoxy(propyl) silane and triethoxy(propyl) silane; form a self-assembly monolayer with the silane on surfaces of the substrate, wherein the self-assembly monolayer containing lipoplex nanoparticles; bind a protein onto the surfaces to form an active site, wherein the protein comprises Protein A; and perform a reaction with antibodies to have an antibody conjugation on the active site, so as to form the antibody immunolipoplex nanoparticle (Ab-ILN) biochip, wherein the antibody conjugation is a ligands-receptors interaction which comprises avidin-biotin, digoxigenin-anti-Dig, fluorescein-anti-FITC and hapten linkages of antibody molecules.

In one example of the second embodiment, the antibodies were as receptors which comprise moieties for binding to target extracellular vesicles, microvesicles, exosomes and circulating cell-free particles which is selected from one of the group consisting of viruses, bacteria and antigens.

In one example of the second embodiment, the lipoplex nanoparticles are lyophilized lipoplex nanoparticles.

In one example of the second embodiment, the lipoplex nanoparticles further comprise molecular beacons, quantum dots, messenger RNA, microRNA, lncRNA, genomic DNA, circulating tumor DNA, drug, DNA/RNA, magnetic particles, Au nanoparticles and proteins.

In one example of the second embodiment, the antibody immunolipoplex nanoparticle (Ab-ILN) biochip is applied for finger prick capillary blood assay.

In a third embodiment, the present invention disclosed a method of fabricating an antibody tethered lipoplex nanoparticle (Ab-TLN) biochip, said method comprises the following steps:

(1). Provide a substrate which comprises glass, silicon wafer, polymer and ceramics; (2). Coat gold onto the substrate to form a gold layer on surfaces of the substrate; (3). Provide a composition which comprises a tethering molecule, a linker which comprises a biotin-conjugated thiol molecule with ethylene oxide unites and a lateral spacer; (4). Form a self-assembly monolayer with the composition on the gold layer, wherein the self-assembly monolayer containing tethered liposomal nanoparticles; (5). Add an avidin which comprises neutravidin and straptavidin to the self-assembly monolayer, wherein the avidin reacts with the linker to form an avidin-modified surface; and (6). Perform a reaction with antibodies to have an antibody conjugation on the avidin-modified surface, so as to form the antibody tethered lipoplex nanoparticle (Ab-TLN) biochip, wherein the antibody conjugation is a ligands-receptors interaction which comprises complementary DNA/RNA, avidin-biotin, digoxigenin-anti-Dig, fluorescein-anti-FITC and hapten linkages of antibody molecules.

In one example of the third embodiment, the tethering molecules comprises 20-tetradecyloxy-3,6,9,12,15,18,22-heptaoxahexatricontane-1-thiol (WC14), 29-hexadecyloxy-3,6,9,12,15,18,21,24,27,31-decaoxaheptatetracontan-1-thiol (FC16), 20-(Z-octadec-9-enyloxy)-3,6,9,12,15,18,22-heptaoxatetracont-31-ene-1-thiol (DC18), and thiolipids with ethylene oxide units.

In one example of the third embodiment, the lateral spacer comprises 2-mercaptoethanol, 6-mercaptohexanol and 16-mercaptohexadecanoic acid.

In one example of the third embodiment, the tethered liposomal nanoparticles were formed from a lipid mixture which comprises 1,2-di-O-octadecenyl-3-trimethylammonium propane (DOTMA), 1,2-dioleoyl-3-trimethylammonium-propane (DOTAP), 3β-[N—(N',N'-dimethylaminoethane)-carbamoyl]cholesterol hydrochloride (DC-Cholesterol), 1,2-di-O-octadecenyl-3-dimethylammonium propane (DODMA), 1,2-dioleoyl-3-dimethylammonium-propane (DODAP), L-α-phosphatidylcholine (EggPC, SoyPC), Cholesterol, 1,2-dipalmitoyl-sn-glycero-3-phosphocholine (DPPC), saturated fatty acid, 1,2-dioleoyl-sn-glycero-3-phosphocholine (DOPC), 1,2-distearoyl-sn-glycero-3-phosphoethanolamine-N-[methoxy(polyethylene glycol)](DSPE-PEG), and PEG phospholipids.

In one example of the third embodiment, the antibodies are receptors which comprise moieties for binding to target extracellular vesicles, microvesicles, exosomes and circulating cell-free particles which is selected from one of the group consisting of viruses, bacteria and antigens.

In one example of the third embodiment, the tethered liposomal nanoparticles are lyophilized liposomal nanoparticles.

In one example of the third embodiment, the tethered liposomal nanoparticles further comprise molecular beacons, quantum dots, messenger RNA, microRNA, lncRNA, genomic DNA, circulating tumor DNA, drug, DNA/RNA, magnetic particles, Au nanoparticles and proteins.

In one example of the third embodiment, the antibody tethered lipoplex nanoparticle (Ab-TLN) biochip is applied for finger prick capillary blood assay.

In still another embodiment, a method of detecting the presence of a disease or condition in a subject is provided, said method comprises the following steps:

(1). Provide a body fluid sample containing membrane proteins and intra-vesicular DNA/RNA/proteins of extracellular vesicles; (2). Provide an antibody-based biochip which comprises an antibody immunolipoplex nanoparticle (Ab-ILN) biochip and an antibody tethered lipoplex nanoparticle (Ab-TLN) biochip; (3). Contact the body fluid sample with the antibody-based biochip, wherein the membrane proteins and the intra-vesicular DNA/RNA/proteins of extracellular vesicles are captured by molecular probes on the antibody-based biochip, wherein the molecular probes comprises molecular beacons and aptarmer beacons; and (4). Characterize the membrane proteins and the intra-vesicular DNA/RNA/proteins of extracellular vesicles by using instrument which comprises TIRF microscope, fluorescence microscope, plate reader, microplate reader and portable fluorescence detector, so as to detect the presence of a disease or condition in the subject.

In one example of this embodiment, the body fluid sample comprises blood, serum, urine, sputum and saliva from the subject.

In one example of this embodiment, the antibody-based biochip is connected to a microfluidic setup, so a cell culture medium or the body fluid sample is able to be brought onto the antibody-based biochip.

In one example of this embodiment, surfaces of the antibody-based biochip have ligands which comprise antibody molecules, peptides, carbohydrates, DNA and RNA, and wherein said ligands being for detecting specific extracellular vesicles surface biomakers.

In one example of this embodiment, the antibody immunolipoplex nanoparticle (Ab-ILN) biochip has lipoplex nanoparticles which comprise reagents being selected from one of the groups or the combinations consisting of molecular beacons, quantum dots, messenger RNA, microRNA, lncRNA, genomic DNA, circulating tumor DNA, drug, DNA/RNA, magnetic particles, Au nanoparticles and proteins.

In one example of this embodiment, the tethered lipoplex nanoparticle (Ab-TLN) biochip has tethered liposomal nanoparticles which comprise reagents being selected from one of the groups or the combinations consisting of molecular beacons, quantum dots, messenger RNA, microRNA, lncRNA, genomic DNA, circulating tumor DNA, drug, DNA/RNA, magnetic particles, Au nanoparticles and proteins.

In one example of this embodiment, the disease or condition comprises a cancer, an antigen and extracellular vesicles derived from a cancer lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colon-rectal cancers, prostatic cancer, pancreatic cancer, and cancer cachexia.

In one example of this embodiment, the antigen comprises extracellular vesicles, exosome, proteins, peptides, and nucleic acids from the cancer.

In accordance with the foregoing summary, the following presents a detailed description of the example of the present invention, which is presently considered the best mode thereof. However, this invention can also be applied extensively to other embodiments, and the scope of this present invention is expressly not limited except as specified in the accompanying claims.

In conclusion, the invention disclosed a method of preparing of antibody-based biochip and their application in detecting the presence of a disease or condition in a subject. In other words, a method of detecting the presence of a disease or condition in a subject obtaining a body fluid sample by capturing and identifying both membrane protein and intra-vesicular DNA/RNA/proteins of EVs using an antibody-based immune lipoplex nanoparticle (Ab-ILN) biochip or array is provided.

Accordingly, one example of the invention is to form an antibody-based biochip on surfaces treatment with an ultrathin gold layer, the steps comprise:

Gold coating of a solid substrate with the substrate being glass, silicon wafer, polymer, ceramics or any solid materials; a thin layer of self-assembly monolayer such as 2-mercaptoethanol, 6-mercaptohexanol, 16-mercaptohexadecanoic acid (MHA), and other thiol-backfiller molecules; linker molecules such as biotin-conjugated thiol molecules with ethylene oxide unites; preparing neutravidin, straptavidin or other avidin-biotin linkages; and preparing biotin-conjugated Protein A treatment for antibody conjugation.

Another example of the invention is to form an antibody-based biochip on surfaces treatment without gold coating, the steps comprise:

A cleaned solid substrate with the substrate being glass, silicon wafer, polymer, ceramics or any solid materials; a thin layer of self-assembly monolayer such as trimethoxy [3-(oxiranylmethoxy)propyl]silane, triethoxy [3-(oxiranylmethoxy)propyl]silane or any epoxy-conjugated silane molecules; a thin mixture layer of self-assembly monolayer with any epoxy-conjugated silanes and other silane-backfiller molecules such as trimethoxy(methyl) silane, trimethoxy (propyl) silane, triethoxy(propyl) silane; and preparing Protein A treatment for antibody conjugation.

For preparing antibody conjugation, the steps comprise: conjugation with antibodies on Protein A treated or untreated surfaces; conjugation with antibodies on gold coated surface or other surfaces; target specific antibodies as receptors comprising one or more surface targeting moieties for binding to target extracellular vesicles, microvesicles, exosomes and circulating cell-free particles including viruses, bacteria or antigens that corresponds to a particular disease or condition.

In the present invention, the ligands contain antibody molecules, peptides, carbohydrates, DNA/RNA or their mixtures as ligands for detecting specific EV surface biomakers.

In the present invention, the antibody conjugation is achieved by Protein A, avidin-biotin, digoxigenin (Dig)-anti-Dig, fluorescein-anti-FITC or other hapten linkages of antibody molecules.

In the present invention, the lipoplex nanoparticles contain reagents or reagent mixtures such as molecular beacons, quantum dots, and/or other sensing molecules and particles as molecular probes for detecting intra-cellular biomarkers such as messenger RNA, microRNA, lncRNA, genomic DNA, circulating tumor DNA and proteins.

In the present invention, the lipoplex nanoparticles contain reagents or reagent mixtures such as drug, DNA/RNA, magnetic particles, Au nanoparticles and/or other therapeutic molecules, imaging molecules and particles.

In the present invention, the Ab-ILN array chip is connected to a microfluidic setup so cell culture medium or human body fluids can be brought onto the array and EV washing can be carried out after certain EV incubation time.

In the present invention, the Ab-ILN biochip or arrays are used for finger prick capillary blood assay.

In the present invention, lyophilized lipoplex nanoparticles can be used for Ab-ILN biochip or arrays.

In the present invention, the body fluid sample is blood, serum, urine, sputum or saliva from the subject.

In the present invention, the Ab-ILN biochips, other ILN biochip, array chips, microarrays and particles capture target microvesicles, exosomes, extracellular vesicles and/or circulating cell-free particles with the contained mRNAs, microRNAs, lncRNAs, circulating genomic DNAs, circulating tumor DNAs and/or proteins being detected by molecular probes such as molecular beacons and aptamer beacons using a total internal reflective fluorescence (TIRF) microscope, fluorescence microscope, plate reader, microplate reader or portable fluorescence detector.

In the present invention, single-EV analysis of co-localization of multiple RNA and membrane protein targets comprise: antibodies on Ab-ILN chip are used to capture a few EVs for single-EV analysis; single-EV analysis can identify co-localization of multiple RNA and membrane protein targets in individual EVs with high sensitivity;

conjugation with antibodies on Ab-ILN is used for both separation and identification of a specific membrane protein on a single EV; conjugation with antibodies on Protein A treated or untreated surfaces; conjugation with antibodies on gold coated surface or other surfaces and target specific antibodies as receptors comprise one or more surface targeting moieties for binding to target extracellular vesicles, microvesicles, exosomes and circulating cell-free particles including viruses, bacteria or antigens that corresponds to a particular disease or condition.

In the present invention, the disease or condition is a cancer and the antigen or EV detected by the LN is derived from a cancer which is selected from the group consisting of lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colon-rectal cancers, prostatic cancer, pancreatic cancer, or cancer cachexia.

In the present invention, the antigen is an EV, exosome, protein, peptide, or nucleic acid from the cancer.

In the present invention, a method of detecting both membrane protein and intravesicular DNA/RNA/proteins of EVs at the single EV basis by using an Ab-TLN biochip is disclosed, the method comprises the following steps:

Surface tethering treatment, the steps comprise:

Au coating of a solid substrate with the substrate being glass, silicon wafer, polymer, ceramics or any solid materials; a thin layer of self-assembly monolayer such as 2-mercaptoethanol, 6-Mercaptohexanol, 16-mercaptohexadecanoic acid (MHA), and other thiol-backfiller molecules; tethering molecules such as lipidic thiol anchor molecule WC14 [20-tetradecyloxy-3,6,9,12,15,18,22-heptaoxahexatricontane-1-thiol], FC16, DC18, and other thiolipids with ethylene oxide units.

Prepare tethered liposomal nanoparticles which comprises: lipid mixtures such as 1,2-di-O-octadecenyl-3-trimethylammonium propane (DOTMA), 1,2-dioleoyl-3-trimethylammonium-propane (DOTAP), 3β-[N—(N',N'-dimethylaminoethane)-carbamoyl]cholesterol hydrochloride (DC-Cholesterol), and other ionizable lipids, 1,2-di-O-octadecenyl-3-dimethylammonium propane (DODMA), 1,2-dioleoyl-3-dimethylammonium-propane (DODAP), and other non-ionizable lipids, L-α-phosphatidylcholine (Egg PC, SoyPC), Cholesterol, 1,2-dipalmitoyl-sn-glycero-3-phosphocholine (DPPC), and other saturated fatty acid, 1,2-dioleoyl-sn-glycero-3-phosphocholine (DOPC), and other helper lipids and 1,2-distearoyl-sn-glycero-3-phosphoethanolamine-N-[methoxy(polyethylene glycol)](DSPE-PEG), and other PEG phospholipids.

In the present invention, the TLN conjugation is achieved by avidin-biotin, complementary DNA/RNA, digoxigenin (Dig)-anti-Dig, fluorescein-anti-FITC or other hapten linkages of antibody molecules or their mixtures.

In the present invention, the ligands contain antibody molecules, peptide, carbohydrate, DNA/RNA or their mixtures as ligands for detecting specific EV surface biomakers.

In the present invention, the lipoplex nanoparticles are used to form Ab-TLN array biochip.

In the present invention, said lipoplex nanoparticles contain reagents or reagent mixtures such as molecular beacons, quantum dots, and/or other sensing molecules and particles as molecular probes for detecting intra-cellular biomarkers such as messenger RNA, microRNA, lncRNA, genomic DNA, circulating tumor DNA and proteins.

In the present invention, said lipoplex nanoparticles contain reagents or reagent mixtures such as drug, DNA/RNA, magnetic particles, Au nanoparticles and/or other therapeutic molecules, imaging molecules and particles.

In the present invention, said Ab-TLN array chip is connected to a microfluidic setup so cell culture medium or human body fluids can be brought onto the array and EV washing can be carried out after certain EV incubation time.

In the present invention, the Ab-TLN biochip or arrays are used to finger prick capillary blood assay.

In the present invention, lyophilized lipoplex nanoparticles can be used to Ab-TLN biochip or arrays.

In the present invention, the body fluid sample is blood, serum, urine, sputum or saliva from the subject.

In the present invention, the Ab-TLN biochips, other TLN biochips, array chips, microarrays and particles capture target microvesicles, exosomes, extracellular vesicles and/or circulating cell-free particles with the contained mRNAs, microRNAs, lncRNAs, circulating genomic DNAs, circulating tumor DNAs and/or proteins being detected by molecular probes such as molecular beacons and aptarmer beacons using a TIRF microscope, fluorescence microscope, plate reader, microplate reader or portable fluorescence detector.

In the present invention, the disease or condition is a cancer and the antigen or EV detected by the LN is derived from a cancer which is selected from the group consisting of lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colon-rectal cancers, prostatic cancer, pancreatic cancer, or cancer cachexia.

In the present invention, the antigen is an EV, exosome, protein, peptide, or nucleic acid from the cancer.

Example 1

Fabricate and Test Ab-ILN Biochip

We show a new biochip design which could simultaneously detect membrane protein targets and intra-vesicular RNA targets of individual EVs.

In one method, a mixture of 1-thiahexa(ethyleneoxide) lipidic anchor molecule WC14 [20-tetradecyloxy-3,6,9,12, 15,18,22-heptaoxahexatricontane-1-thiol], biotin-PEG-SH and a lateral spacer β-mercaptoethanol (βME) in ethanol was added onto a gold coated glass substrate to form self-assembly monolayers (SAMs). Avidin was then added and un-reacted avidin was washed away using PBS. The biotin-conjugated Protein A was bound on the avidin-modified substrate surface through biotin-avidin interactions and the unbound Protein A was washed away with PBS. A target-specific antibody was then added and un-reacted antibody was washed away using PBS. The antibody-modified biochip can be used as an Ab-ILN biochip as shown in the first step of FIG. 1A.

We can tether antibodies on the chip surface to capture the EVs presenting the target receptor as shown in FIG. 1A. Our previous works on protein chips and immune-nanoparticles-based gene delivery showed that bioactivity of tethered antibodies could increase >100 times when non-specific binding was minimized by using Protein A, PEG linkers and PEG spacers. We have optimized these design parameters to achieve high EV binding at low antibody consumption.

The Ab-ILN biochips only captured the Ab-specific EVs, while other EVs could be washed away.

After washing away unbound EVs, we applied cationic LNs containing MBs of the RNA targets, say miR-21, to the chip. If captured EVs contain miR-21, the MB would report a fluorescence signal after the fusion between LNs and EVs. This concept is explained schematically in FIG. 1A.

FIG. 1B shows the results of using anti-CD-63 to capture CD-63-rich EVs and some, but not all, captured CD-63-rich EVs are rich in miR-21. The total internal reflective fluorescence (TIRF) microscope images demonstrate that the assay can distinguish the differences in EV-enriched TTF-1 mRNA among four Stage I lung cancer plasma samples.

The Ab-ILN biochip and a TLN biochip described in our previous patent application (US 20140094383) were used to test the same Stage I lung cancer plasma samples, and the results are compared in FIG. 1C. The results from four Stage I lung cancer patients show a similar trend in the two assays.

Example 2

Fabricate and Test Ab-TLN Biochip

Figure 2:
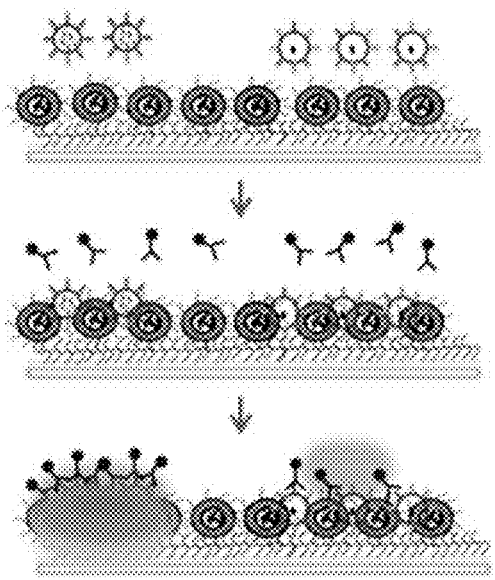
FIG. 2.(A) Schematic of an Ab-TLN biochip design for EV capturing by tethered cationic lipoplex nanoparticles and detection of intra-vesicular RNAs by MPs in the lipoplex nanoparticles, followed with the detection of surface membrane proteins using first antibody and then fluorescence labelled second antibody.
Figure 2:
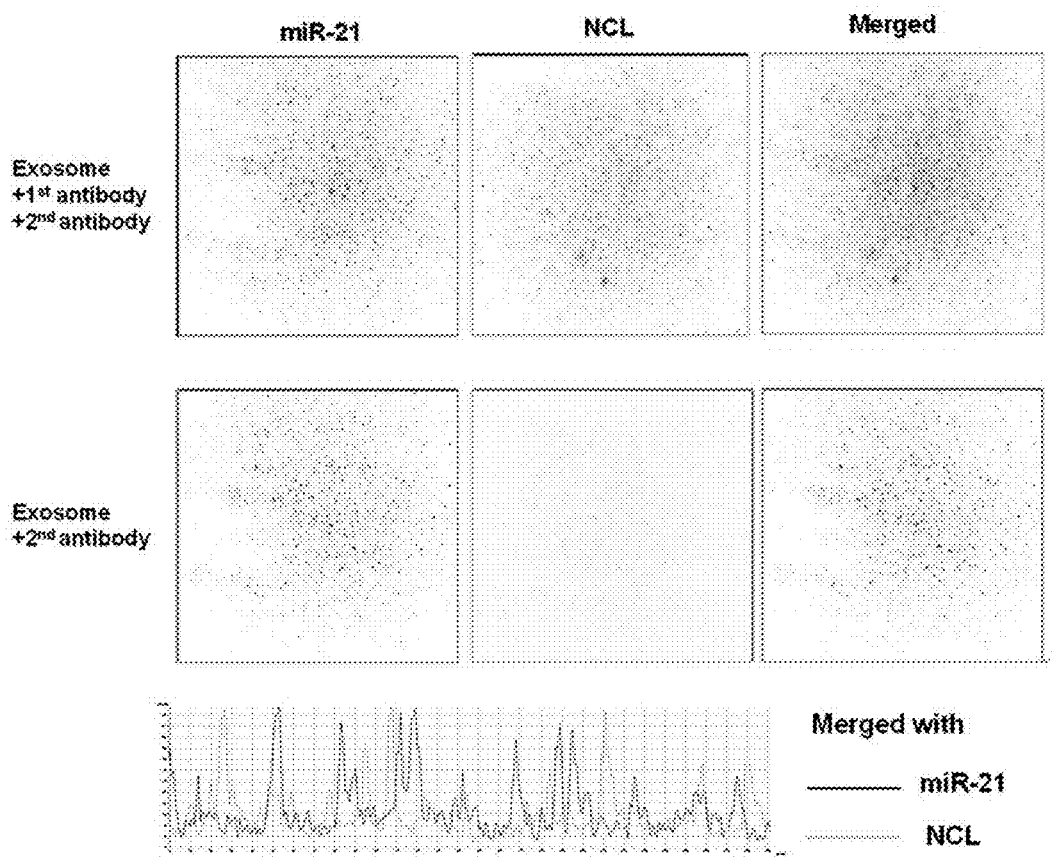

FIG. 2A shows the schematic of an Ab-TLN biochip design for EV capturing by tethered cationic lipoplex nanoparticles and detection of intra-vesicular RNAs by MPs in the lipoplex nanoparticles, followed with the detection of surface membrane proteins using first antibody and then fluorescence labeled second antibody.

EVs from culture supernatants of $2 \times 10^7$ cells or 20 μL plasma samples were captured by an Ab-TLN biochip which consists of either empty liposomes or liposomes containing RNA-specific MBs (e.g. miR-21). After the fusion of negatively charged EVs with positively charged cationic LNs, a TIRF microscope was used to measure the surface receptors of captured EVs by fluorescence labelled antibody and RNA targets inside the captured EVs by the RNA-specific MBs. Using two different fluorescent molecules as shown in FIG. 2B, e.g. FAM (green) and Cy5 (red), the co-localization of both the RNA target and the surface receptor for individual EVs can be identified via the compounded images.

FIG. 2B shows nucleolin (NCL) EV surface proteins and EV-encapsulated miR-21 identified by our Ab-TLN chip for a pancreatic cancer cell line. The overlapping peaks show co-localization of both miR-21 and NCL protein in the same EVs.

Example 3

Ab-ILN Biochip Showing Single-EV Analysis of Co-localization of RNA and Membrane Protein Targets We demonstrate single-EV analysis of co-localization of multiple RNA and membrane protein targets.

Our ILN biochip can be used to identify a membrane protein target and 1-2 RNA targets in a single EV.

Figure 3:
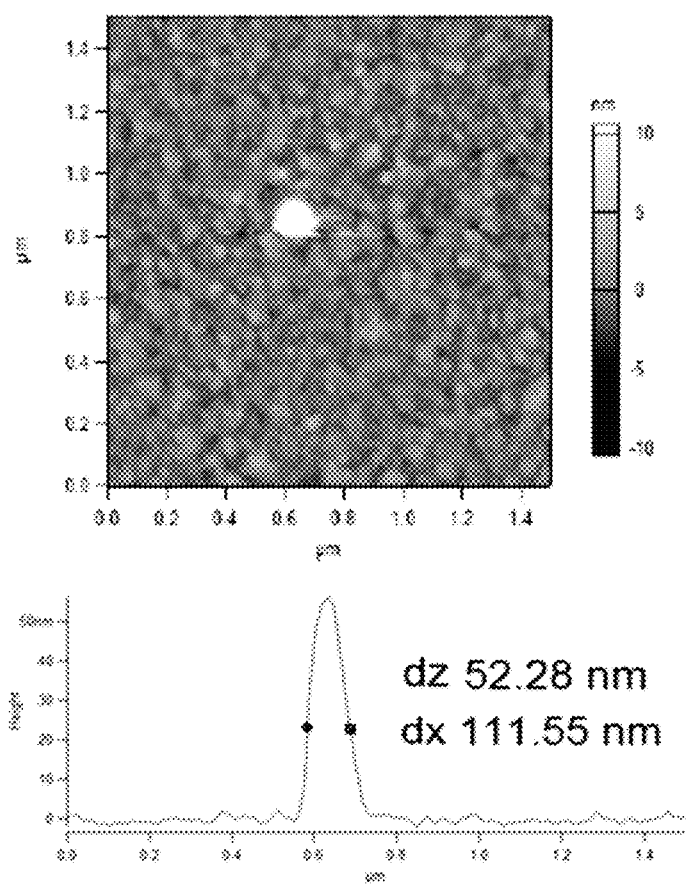
FIG. 3.(A) Ab-ILN biochip showing single-EV analysis of co-localization of RNA and membrane protein targets. Atomic Force Microscope (AFM) image of a single captured EV by Ab-ILN biochip.
Figure 3:
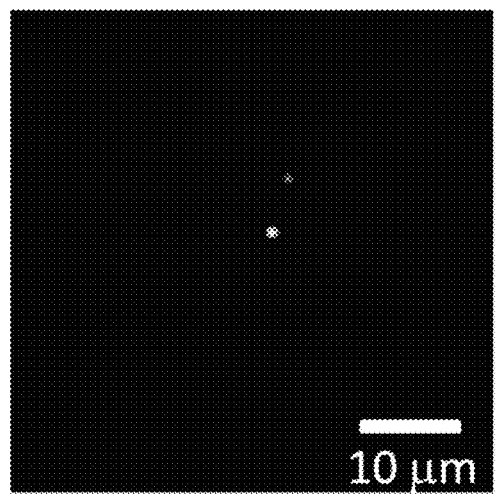
Figure 3:
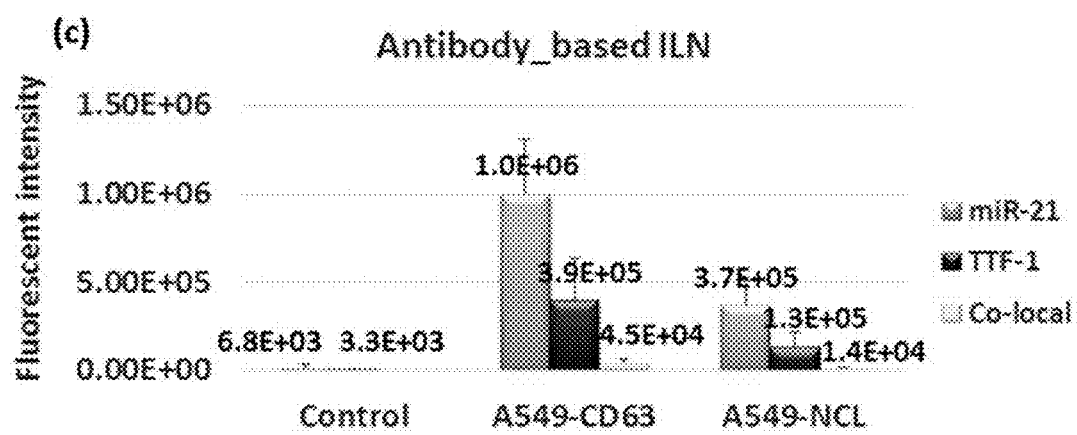

FIG. 3A shows a biological atomic force microscopy (Bio-AFM) image of single EV secreted by A549 lung cancer cells captured by anti-CD63 antibody in aqueous solution. The diameter of this CD63-rich EV is ~100 nm.

FIG. 3B shows a TIRF microscopy image of two miR-21-rich EVs with CD63 membrane proteins. The green fluorescent signal reports the fusion of LNs containing miR-21-specific MBs with the captured EVs.

We compare CD63-rich and NCL-rich EVs with miR-21 and TTF-1 content from A549 cell secreted EVs as shown in FIG. 3C. There are more EVs containing CD63 than NCL surface receptor, and a small fraction (12.2 and 10.9% for CD63 and NCL EVs, respectively) of those EVs contains both miR-21 and TTF-1 mRNA. This is the first time that both membrane protein and intra-vesicular RNA targets of individual EVs are detected on a single chip.

Example 4

Figure 4:
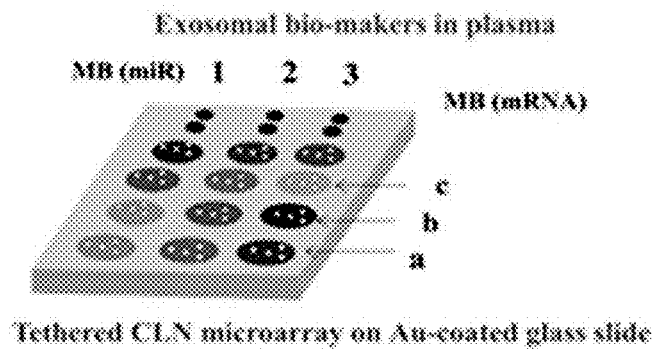
FIG. 4.(A) Schematic of multiplexing ILN/TLN array biochips for analysis of miRNA, mRNA and membrane protein target profiling in a single assay. This array design can also be designed for the Ab-ILN chips by placing different antibodies in the small areas for EV surface receptor profiling.
Figure 4:
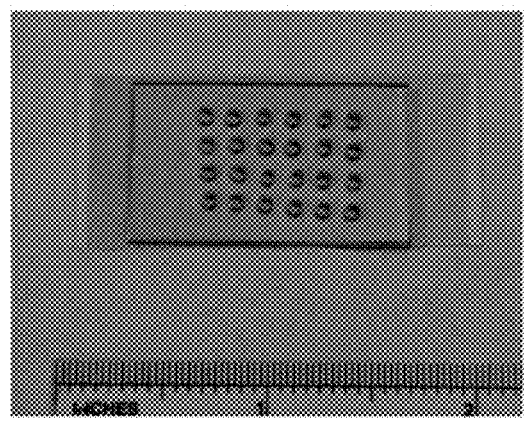
Figure 4:
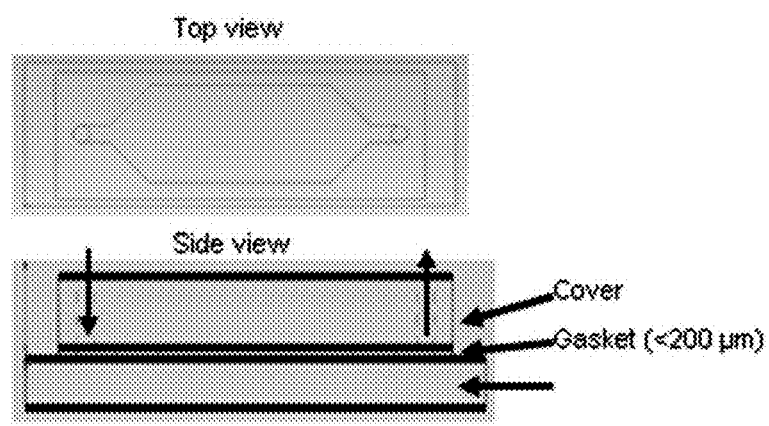

Multiplexing ILN/TLN Array Biochips for Analysis of a Large Number of MicroRNA, Messenger RNA and Membrane Protein Targets The ILN/TLN biochip can be extended to an array type design as shown in FIG. 4 where each spot in the ILN array contains LNs with 2 RNA-specific MBs, one with green (FAM) and the other with red (Cy5) fluorescence dyes inside each LN.

Such a multiplexing array allows capture and the detection of >300 RNA targets in a single sample within 2 hours of assay time. Our data (not shown) indicate that fluorescence background would remain unchanged on chip for at least 4 hours.

For most applications, we suggest to test an array for ~100 RNA and membrane protein targets. Each ILN spot in the 10×10 array is 0.5 mm in diameter and ~50 μL of sample (cell culture media or patient plasma) is sufficient for the entire array. Here, 20 images (80 μm×80 μm for each image area) taken within 25 seconds, instead of 100 images taken in 2 minutes for each MB as in our standard ILN assay, are used to keep the sample size small and the assay time short.

Although the fluorescence signal variation of 20-image average is slightly larger than that of the 100-image average, it should be acceptable for the profiling purpose. In comparison, a typical qRT-PCR assay requires collecting total RNA from >100-200 μL of plasma sample for either single or ~10 RNA targets.

This ILN array design can also be designed by placing different antibodies in the small areas for EV surface receptor profiling.

Example 5

Figure 5:
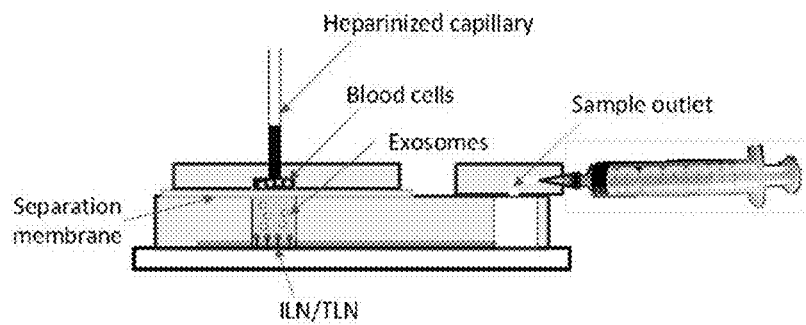
FIG. 5. (A) Schematic of a whole blood ILN or TLN biochip design.
Figure 5:
Figure 5:
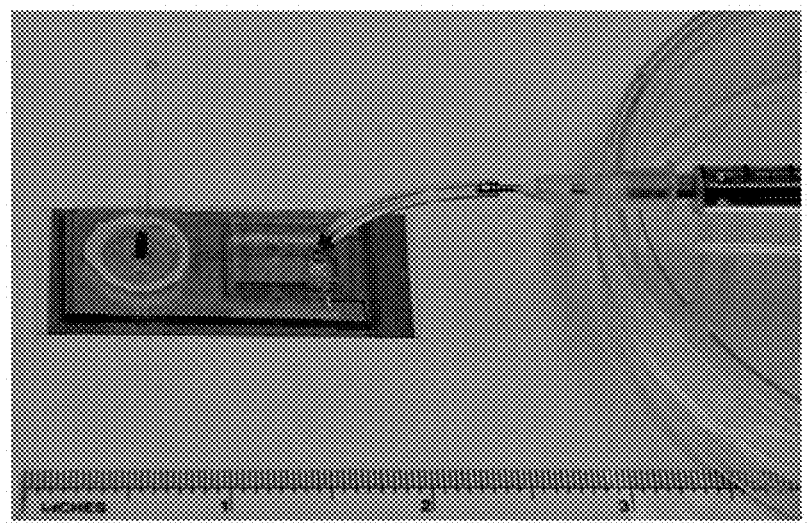

Design of Finger Prick Whole Blood Assay by Using ILN or TLN Biochip for Disease Detection We have demonstrated a simple whole blood ILN/TLN biochip design which does not need any sample preparation procedure. FIG. 5A shows the schematic of a whole blood ILN or TLN biochip design.

FIG. 5B shows a photograph of blood droplet collection by a capillary using a finger pricker. The amount of blood collected can be controlled from 0.5 to 30 µL using a depth of lancet.

FIG. 5C shows a typical whole blood ILN or TLN biochip. The typical whole blood ILN/TLN biochip consists of a double asymmetric membrane filter to remove peripheral blood cells, micro-channels on a silicon-based elastomeric polymer such as PDMS, and a syringe with a flow rate controller.

Example 6

Lyophilization of Lipoplex Nanoparticles for Long-Term Storage

Figure 6:
FIG. 6. Photograph of two bottles of lyophilized lipoplex nanoparticles for long term storage using a freeze-drying method such as lyophilization of FDA approved drugs.

Here, we demonstrate lyophilization of free CLN nanoparticles for extending shelf life of LNs as shown in FIG. 6. The freeze-drying method used follows the FDA-approved drug manufacturing procedure.

The lyophilized LNs can be used for the Ab-ILN/Ab-TLN biochip or array.

The Ab-ILN and Ab-TLN assay can provide the co-localization of both the target RNA and the surface receptor for individual EVs via the merged images.

The Ab-ILN/Ab-TLN biochips can detect EVs with tumor-specific membrane proteins and intra-vesicular RNAs.

The finger prick whole blood ILN/TLN biochips are very easy to use and require a very small amount of blood sample.

Lyophilization of lipoplex nanoparticles can provide long-term storage of ILN/TLN biochips.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of detecting a presence of leukemia or multiple myeloma in a subject, the method comprising:
   (a) providing a body fluid sample comprising extracellular vesicles, wherein the extracellular vesicles comprise:
      i. cancer-specific membrane proteins; and
      ii. intra-vesicular RNA;
   (b) providing an antibody-coated biochip surface;
   (c) contacting the body fluid sample with the antibody-coated biochip surface, such that the extracellular vesicles comprising i. cancer-specific membrane proteins; and ii. intra-vesicular RNA are preferentially captured on the antibody-coated biochip surface, thereby obtaining captured extracellular vesicles bound to the antibody-coated biochip surface; and
   (d) detecting the intra-vesicular RNA of the captured extracellular vesicles bound to the antibody-coated biochip surface by applying lipoplex nanoparticles comprising molecular beacons to the antibody-coated biochip surface.

2. The method according to claim 1, wherein the body fluid sample comprises a body fluid selected from the group consisting of: blood and serum.

3. The method according to claim 1, wherein the body fluid sample is a serum sample.

4. The method according to claim 1, wherein the body fluid sample is a plasma sample.

5. The method according to claim 1, further comprising flowing the body fluid sample through a microfluidic device fluidly connected to the antibody-coated biochip surface.

6. The method according to claim 1, wherein the lipoplex nanoparticles comprising molecular beacons further comprise reagents selected from the group consisting of: quantum dots, magnetic particles, Au nanoparticles, and combinations thereof.

7. The method according to claim 1, wherein obtaining captured extracellular vesicles bound to the antibody-coated biochip surface further comprises washing away extracellular vesicles not bound to the antibody-coated biochip surface.

8. The method according to claim 1, further comprising:
   (e) characterizing a fluorescence expression of the captured extracellular vesicles bound to the antibody-coated biochip surface and the applied lipoplex nanoparticles comprising molecular beacons.

9. The method according to claim 8, wherein the fluorescence expression is characterized using an instrument selected from the group consisting of: a total internal reflection fluorescence (TIRF) microscope, a fluorescence microscope, a plate reader, a microplate reader, and a portable fluorescence detector.

10. The method according to claim 9, wherein the fluorescence expression is characterized using a fluorescence microscope.

11. The method according to claim 1, wherein the extracellular vesicles comprise exosomes.

12. The method according to claim 1, wherein the extracellular vesicles are exosomes comprising:
   i. CD63 or nucleolin; and
   ii. intravesicular mRNA or microRNA.

13. The method according to claim 1, wherein (d) comprises detecting intravesicular messenger RNA or intravesicular lncRNA.

14. The method according to claim 1, wherein (d) comprises detecting intravesicular microRNA.

15. The method according to claim 1, wherein the method is for detecting a presence of leukemia.

16. The method according to claim 1, wherein the method is for detecting a presence of multiple myeloma.

* * * * *